(12) United States Patent
Barnes et al.

(10) Patent No.: US 10,987,363 B2
(45) Date of Patent: Apr. 27, 2021

(54) FLUTICASONE FUROATE IN THE TREATMENT OF COPD

(71) Applicant: GLAXOSMITHKLINE INTELLECTUAL PROPERTY DEVELOPMENT LIMITED, Brentford (GB)

(72) Inventors: Neil Christopher Barnes, Uxbridge (GB); Steven John Pascoe, Research Triangle Park, NC (US)

(73) Assignee: GLAXOSMITHKLINE INTELLECTUAL PROPERTY DEVELOPMENT LIMITED, Brentford (GB)

( * ) Notice: Subject to any disclaimer, the term of this patent is extended or adjusted under 35 U.S.C. 154(b) by 0 days.

(21) Appl. No.: 15/313,769

(22) PCT Filed: May 27, 2015

(86) PCT No.: PCT/EP2015/061765
§ 371 (c)(1),
(2) Date: Nov. 23, 2016

(87) PCT Pub. No.: WO2015/181262
PCT Pub. Date: Dec. 3, 2015

(65) Prior Publication Data
US 2017/0189424 A1 Jul. 6, 2017

Related U.S. Application Data

(60) Provisional application No. 62/042,506, filed on Aug. 27, 2014, provisional application No. 62/004,304, filed on May 29, 2014, provisional application No. 62/003,764, filed on May 28, 2014.

(51) Int. Cl.
| | | |
|---|---|---|
| *A61K 31/58* | (2006.01) | |
| *A61K 31/439* | (2006.01) | |
| *A61K 9/00* | (2006.01) | |
| *A61K 31/138* | (2006.01) | |
| *G01N 33/50* | (2006.01) | |

(52) U.S. Cl.
CPC ............ *A61K 31/58* (2013.01); *A61K 9/0075* (2013.01); *A61K 31/138* (2013.01); *A61K 31/439* (2013.01); *G01N 33/5091* (2013.01); *G01N 2800/122* (2013.01); *G01N 2800/52* (2013.01)

(58) Field of Classification Search
CPC .... A61K 31/58; A61K 31/138; A61K 31/469; A61K 9/0075
See application file for complete search history.

(56) References Cited

U.S. PATENT DOCUMENTS

| | | |
|---|---|---|
| 5,873,360 A | 2/1999 | Davies et al. |
| 7,101,866 B2 | 9/2006 | Biggadike et al. |
| 7,488,827 B2 | 2/2009 | Laine et al. |
| 8,534,281 B2 | 9/2013 | Davies et al. |
| RE44,874 E | 4/2014 | Box et al. |
| 9,750,726 B2 | 9/2017 | Baker et al. |
| 2007/0062525 A1 | 3/2007 | Bonney et al. |
| 2008/0196718 A1 | 8/2008 | Connell et al. |
| 2012/0309725 A1 | 12/2012 | Baker et al. |

FOREIGN PATENT DOCUMENTS

| | | |
|---|---|---|
| GB | 2242134 | 9/1991 |
| WO | WO 02/12265 | 2/2002 |
| WO | WO 03/024439 | 3/2003 |
| WO | WO 2005/104745 | 11/2005 |
| WO | WO 2007/012871 | 2/2007 |
| WO | WO 2007/068896 | 6/2007 |
| WO | WO 2011/067212 * | 6/2011 |
| WO | WO 2012/168161 A1 | 12/2012 |
| WO | WO 2014/027045 | 2/2014 |

OTHER PUBLICATIONS

Bafadehl et al. in Am J Respir Crit Care Med 186(1), 48-55 (2012).*
Dransfield et al. The Lancet, Respiratory Medicine 1(3), 210-223 (2013) (Year: 2013).*
Brightling et al. in Thorax 60:193-198 (2005) (Year: 2005).*
Burge PS et al. BMJ 2000; 320: 297-303 (Year: 2000).*
Brightling CE, et al. Sputum eosinophilia and short-term response to prednisolone in chronic obstructive pulmonary disease: a randomised controlled trial. Lancet 2000; 356: 1480-1485.
Burge PS, et al. Randomised, double blind, placebo controlled study of fluticasone propionate in patients with moderate to severe chronic obstructive pulmonary disease: the ISOLDE trial. BMJ 2000; 320: 1297-1303.
Chanez P, et al. Corticosteroid reversibility in COPD is related to features of asthma. Am J Respir Crit Care Med 1997; 155: 1529-1534.
Global Initiative for Chronic Obstructive Lung Disease 2018 Report.
Hospers JJ, et al. Asthma attacks with eosinophilia predict mortality from chronicobstructive pulmonary disease in a general population sample. Am J Respir Crit Care Med 1999; 160: 1869-1874.
Leigh, R, et al., "Stable COPD: predicting benefit from high-dose inhaled corticosteroid treatment", Eur Respir J 2006; 27: 964-971, DOI: 10.1183/09031936.06.00072105, Copyright ERS Journals Ltd 2006.

(Continued)

*Primary Examiner* — Dennis Heyer
(74) *Attorney, Agent, or Firm* — James P. Riek

(57) ABSTRACT

The present invention relates to pharmaceutical products comprising fluticasone furoate for use in the treatment of COPD patients, particularly a subgroup of COPD patients that through analysis have been identified as possessing an eosinophil blood count of ≥150 cells/µl. The present invention is further directed to methods for treating a patient with COPD which methods include identifying a patient that will respond to treatment and administering a pharmaceutical product of the present invention comprising fluticasone furoate to said patient.

31 Claims, No Drawings

(56) References Cited

OTHER PUBLICATIONS

Manson, SC, et al, the Cumulative Burden of oral corticosteroid side effects and the economic implications of steroid use. Resp Med 2009; 103(7): 975-94.

McDonald VM, et al. Multidimensional assessment and tailored interventions for COPD: respiratory utopia or common sense? Thorax 2013; 68: 691-694.

Pascoe S, et al. Blood eosinophil count as a biomarker of ICS effectiveness inreducing exacerbation rates in COPD. Eur Respir J 2014; 44: Suppl. 58, p. 2817.

Renkenema TE, et al., "Effects of Long-term treatment of corticosteroids in COPD." Chest 1996; 109(5): 1156-62.

Rice KL, et al., "Withdrawal of chronic systemic corticosteroids in patients with COPD: a randomized trial." Am j Respir Crit Care Med 2000; 162(1): 174-8.

Siddiqui S, et al. Blood eosinophils: a biomarker of response to extrafine beclomethasone/formoterol in chronic obstructive pulmonary disease. Am J Respir Crit Care Med 2015; 192: 523-525.

Siva R, et al. Eosinophilic airway inflammation and exacerbations of COPD: a randomised controlled trial. Eur Respir J 2007; 29: 906-913.

Walters JA, et al., Systemic corticosteroids for acute exacerbations of chronic pulmonary disease. Cochrane Database Syst Rev 2014; (9): CD001288.

Neil C. Barnes et al: "Blood eosinophils as a marker of response to inhaled corticosteroids in COPD", European Respiratory Journal, vol. 47, No. 5, Feb. 25, 2016 (Feb. 25, 2016), pp. 137 4-1382, XP055522832, ISSN: 0903-1936, DOI: 10.1183/13993003.01370-2015.

Lee, et al., "Treatment of Stable Chronic Obstructive Pulmonary Disease: the GOLD Guidelines." Amer Family Phys; 2013; vol. 88(10) pp. 655-663F.

Pizzichini, et al., Sputum eosinophilia predicts benefit from prednisone in smokers with chronic obstructive bronchitis. Am J Respir Crit Care Med; 1998; vol. 158; pp. 1511-1517.

Shim, et al., "Response to corticosteroids in chronic bronchitis" J Allergy Clin Immunol; 1978; vol. 62; pp. 363-367.

Qureshi, et al. "Chronic obstructive pulmonary disease exacerbations: latest evidence and clinical implications." Ther Adv Chronic Dis.; 2014; vol. 5(5); pp. 212-227.

Mona Bafadhel et al: "Blood Eosinophils to Direct Corticosteroid Treatment of Exacerbations of Chronic Obstructive Pulmonary Disease",American Journal of Respiratory Andcritical Care Medicine, vol. 186, No. 1, Jul. 1, 2012 (Jul. 1, 2012), pp. 48-55.

Pasc0e Steven et al: "Blood eosinophil counts, exacerbations, and response to the addition of inhaled fluticasone furcate to vilanterol in patients with chronic obstructive pulmonary disease: a secondary analysis of data from two parallel randomised controlled trials.", The Lancet. Respiratory Medicine Jun. 2015, vol. 3, No. 6, Apr. 13, 2015 (Apr. 13, 2015), pp. 435-442.

Dransfield et al., "Once-daily inhaled fluticasone and vilanterol versus vilanterol only for prevention of exacerbations of COPD: two replicate double-blind, parallel-group randomized controlled trials" The Lancet Respiratory medicine 1023; 2013; 1(3):210-23.

Magnussen et al. "Withdrawal of inhaled glucocorticoids and exacerbations of COPD", N England J of Medicine 2014; 371 (14): 1265-94.

P. M. Tweedale et. al., "Short term variability in FEV1 and bronchodilator responsiveness in patients with obstructive ventilatory defects" Thorax 1987, 42, 487-490.

A. Mathioudakis, P. Foden and J. Vestbo "Blood eosinophil count (EOS) can accurately predict responsiveness to inhaled corticosteroids (ICB) in COPD, but only if measured while patients are not receiving steroids" European Respiratory Journal 2018 52: Suppl. 62, OA2125.

European Medicines Agency "Note for guidance on statistical principles of clinical trials" CPMP/ICH/363/96 2006.

P.S. Burge et. al., "Randomised, double blind, placebo controlled study of fluticasone propionate in patients with moderate to severe chronic obstructive pulmonary disease: the ISOLDE trial" British Medical Journal 2000, 320, 1297-1303.

GOLD "Global strategy for the diagnosis management, and prevention of chronic obstructive pulmonary disease" 2013 Global Initiative for Chronic Obstructive Disease.

R. Trivedi et. al., "Umeclidinium in patients with COPD: a randomised, placebo-controlled study" Eur Respir J 2014, 43, 72-81.

F.J. Martinez et. al., "Fluticasone furoate/vilanterol (100/25; 200/25mg) improves lung function in COPD: A randomised trial" Respiratory Medicine 2012, 107, 550-559.

AJRCCM Articles in Press. Published on Mar. 23, 2012 as doi: 10.1164/rccm.201108-1553OC, Blood eosinophils to direct corticosteroid treatment of exacerbations of COPD: a randomized placebo controlled trial; Mona Bafadhel, et al.

BREO ELLI PTA Leaflet, 2013, Summary of product characteristics.

Vestbo, et al., "Pulmonary Perspective/ Global Strategy for the Diagnosis, Management, and Prevention of Chronic Obstructive Pulmonary Disease / GOLD Executive Summary" Am J Respir Crit Care Med vol. 187, Iss. 4, pp. 347-365, Feb 15, 2013.

Global Initiative for Chronic Obstructiive Lung Disease (GOLD); Global Strategy for the Diagnosis, Management and Prevention of COPD, updated 2013..

Lacoste J-Y, "Eosinophilic and neutrophilic inflammation in asthma, chronic bronchitis, and chronic obstructive pulmonary disease" Allergy Clin Immunol, 1993; 92:537-48.

Alonso, JLI, et al., "The Excessive Use of Inhaled Corticosteroids in Chronic Obstructive Pulmonary Disease", Arch Bronconeumol. 2012;48(6):207-212.

Falk, J., et al, "Inhaled and Systemic Corticosteroids in Chronic Obstructive Pulmonary Disease", Proc Am Thorac Soc vol. 5. pp. 506-512, 2008.

Bafadhel, M., et al, AJRCCM Articles in Press. Published on Jun. 16, 2011 as doi:10.1164/rccm.201104-05970C, Acute exacerbations of COPD: identification of biological clusters and their Biomarkers, pp. 1-74.

Donaldson, GC, et al., "Relationship between exacerbation frequency and lung function decline in chronic obstructive pulmonary disease", Thorax 2002;57:847-852.

Gladysherva, E, et al, "Influencing the decline of lung function in COPD:use of pharmacotherapy" International Journal of COPD 2010:5 153-164.

Wouters E FM, et al., "Withdrawal of fluticasone propionate from combined salmeterol/fluticasone treatment in patients with COPD. causes immediate and sustained disease deterioration: a randomised controlled trial", *Thorax*2005;60:480-487.

Jones, et al, "Disease severity and the effect of fluticasone propionate on chronic obstructive pulmonary disease exacerbations", Eur Respir J 2003; 21: 68-73.

Meijer R J., et al, "Effects of inhaled fluticasone and oral prednisolone on clinical and inflammatory parameters in patients with asthma", Thorax 1999;54:894-899.

Martinez, F J, et al., "Fluticasone furoate/vilanterol ( 100/25; 200/25 mg) improves lung function in COPD: A randomised trial", Respiratory Medicine, vol. 107, Issue 4, pp. 550-559, Apr. 1, 2013.

Calverley, P, Pro-Con Editorials, "Inhaled Corticosteroids Are Beneficial in Chronic Obstructive Pulmonary Disease", Am J Respir Crit Care Med vol. 161. pp. 341-344, 2000.

Woods, A.J., et al., "Corticosteroids in the treatment of acute exacerbations of chronic obstructive pulmonary disease", International Journal of COPD 2014:9 421—430.

GSK letter to EPO "Re: European Patent Application No. 15 726 106.6" dated Mar. 15, 2008.

Statement of Opposition filed by Teva UK Limited to EP 3148521 (European Patent Application No. 15726106.6) on Sep. 8, 2020.

Statement of Opposition filed by Gill Jennings & Every LLP to EP 3148521 (European Patent Application No. 15726106.6) on Sep. 8, 2020.

\* cited by examiner

FLUTICASONE FUROATE IN THE TREATMENT OF COPD

CROSS REFERENCE TO RELATED APPLICATIONS

This application is a 371 of International Application No. PCT/EP2015/061765, filed 27 May 2015, which claims the benefit of U.S. provisional applications 62/003,764, filed 28 May 2014; 62/004,304, filed 29 May 2014, and; 62/042,506, filed 27 Aug. 2014, each of which are hereby incorporated by reference in their entirety.

TECHNICAL FIELD OF THE INVENTION

The present invention relates to pharmaceutical products comprising fluticasone furoate for use in the treatment of COPD patients, particularly a subgroup of COPD patients that possess a blood eosinophil count of, for example, ≥150 cells/µl. The present invention is further directed to methods for treating a patient with COPD which method includes identifying a patient that will respond to treatment and administering a pharmaceutical product of the present invention comprising fluticasone furoate to said patient.

BACKGROUND TO THE INVENTION

Chronic Obstructive Pulmonary Disease (COPD), a leading cause of morbidity and mortality worldwide, is characterised by persistent airflow limitation that is typically progressive and associated with an enhanced chronic inflammatory response in the airways to noxious particles or gases. Symptoms of COPD include dyspnea, chronic cough or the production of sputum and spirometry analysis is typically required to confirm diagnosis. A post-bronchodilator $FEV_1/FVC<0.70$ confirms the presence of airflow limitation and thus COPD. A number of factors have been identified that influence the development and progression of COPD, the most studied of which is smoking tobacco cigarettes. Other factors include for example infection, genetics and exposure to particles, such as occupational dusts, chemical agents and pollution from heating fuels.

COPD can be mild to very severe and assessment of the disease is necessary for administration of the appropriate medication to control and/or relieve symptoms. An assessment of a patient's symptoms may include, for example, the COPD Assessment Test (CAT), the COPD Control Questionnaire (CCQ), the St. George's Respiratory Questionnaire (SGRQ) test, Forced Expiratory Volume ($FEV_1$) analysis, and an assessment of their exacerbation risk.

A number of medications are available for the treatment of COPD and these are used mainly to reduce symptoms and reduce the frequency and severity of exacerbations and can include bronchodilators, such as $beta_2$-agonists and anticholinergics, corticosteroids (oral and inhaled), PDE-4 inhibitors, methylxanthines and combinations of some of the above. Bronchodilator medications are vital to symptom management in COPD and the choice between monotherapy with a $beta_2$-agonist, anticholinergic or theophylline, or combination therapy is dependent upon how effective the medication controls a patient's symptoms.

According to the 2014 Global Initiative for Chronic Obstructive Lung Disease (GOLD) strategy, for a patient with few to more significant symptoms but a low risk of exacerbations, bronchodilators are the recommended initial therapy (short-acting if the patient has few symptoms and long-acting if the patient has more pronounced symptoms). For COPD patients with a high risk of exacerbations, inhaled corticosteroids are recommended in combination with a $beta_2$-agonist or anticholinergic.

WO2011/067212/US 2012-309725 describes the combination of the muscarinic antagonist umeclidinium bromide with the $beta_2$-agonist vilanterol trifenatate, which has recently been approved in the US for the treatment of COPD. WO2011/067212 further describes the triple combination therapy of umeclidinium bromide, vilanterol trifenatate and fluticasone furoate for use in the treatment of COPD.

There is also interest in personalised medicine in COPD through the identification of biomarkers that can be used to select a particular population of COPD patients that will derive most benefit from a pharmacologic treatment. For example, studies have shown that COPD patients with different levels of eosinophils in induced sputum and blood can respond differently to certain corticosteroids (Brightling et al, Lancet 2000; 356: 1480-85; Pizzichini et al, Am J Respir Crit Care Med, Vol 158. Pp-1511-1517, 1998; Kitaguchi et al, International Journal of COPD 2012: 7, 283-289). Greater improvements were observed in patients who had higher eosinophil counts compared to patients with lower counts.

Studies have further investigated whether sputum and blood eosinophil counts can be used to direct corticosteroid treatment of exacerbations in COPD (Bafadhel et al, Am J Respir Crit care Med, Vol 186, Iss. 1, pp 48-55, Jul. 1, 2012; Siva et al, Eur Respir J 2007; 29: 906-913).

Despite the research that has been performed in this area to date, there exists a need for further, improved therapies for use in the treatment of COPD patients with a certain level of eosinophils in the lungs.

Furthermore, studies to date that have investigated the benefit of corticosteroid treatment in COPD patients with high and low eosinophil counts have assessed short-term effects such as improvement in $FEV_1$ or reduction in the frequency of exacerbations. No studies appear to investigate or discuss whether corticosteroid therapy can have an impact on lung function decline, the hallmark of the disease, in a subpopulation of COPD patients with a certain eosinophil count. In fact, the GOLD strategy states that, for COPD patients generally, prescription medicines are used to reduce symptoms, reduce frequency and severity of exacerbations, and improve health status and exercise tolerance, but that none of the existing treatments have been shown conclusively in clinical studies to modify the long-term decline in lung function that is characteristic of the disease.

Thus, there is a further need for therapies for use in the treatment of COPD in individual members of the subpopulation of COPD patients, wherein those therapies are able to reduce the rate of decline in lung function.

SUMMARY OF THE INVENTION

The present invention relates to pharmaceutical products comprising fluticasone furoate for use in the treatment of COPD patients, particularly individual members of a subgroup of COPD patients that through analysis have been identified as possessing an eosinophil blood count of ≥150 cells/µl.

In one embodiment, the present invention is directed to a pharmaceutical product comprising fluticasone furoate for use in the treatment of COPD in a patient, wherein the patient has a blood eosinophil count of ≥150 cells/µl, wherein the pharmaceutical product reduces the rate of decline in lung function in a COPD patient.

The present invention is further directed to methods for treating a patient with COPD which methods include identifying a patient that will respond to treatment and administering a pharmaceutical product of the present invention comprising fluticasone furoate to said patient.

DETAILED DESCRIPTION OF THE INVENTION

Definitions

As used herein, the term "fluticasone furoate" refers to 6α,9α-difluoro-17α-[(2-furanylcarbonyl)oxy]-β-hydroxy-16α-methyl-3-oxo-androsta-1,4-diene-17β-carbothioic acid S-fluoromethyl ester, an inhaled corticosteroid that has been shown in clinical studies to be well-tolerated and suitable for once-daily administration in the treatment of asthma and COPD. Fluticasone furoate in combination with vilanterol trifenatate has recently been approved for the once-daily treatment of COPD in the US and asthma and COPD in Europe. Fluticasone furoate is described in WO02/12265/ U.S. Pat. No. 7,101,866, which is incorporated by reference herein. Fluticasone furoate may be abbreviated to "FF".

As used herein, the term "lung function" refers to a COPD patient's forced expiratory volume in 1 second ($FEV_1$). $FEV_1$ is the volume of air exhaled during the first second of maximal forced expiration starting from a position of full inspiration. Lung function in healthy persons declines as a result of the natural aging process. In COPD patients, lung function declines at an accelerated rate. Decline in lung function may be measured in terms of millilitres per year (ml/year). The pharmaceutical products of the present invention comprising fluticasone furoate are intended to reduce the rate of decline in lung function in a patient with COPD, when compared to the same product without fluticasone furoate. Use of the phrase "reduces the rate of decline in lung function" herein in connection with a pharmaceutical product of the present invention comprising fluticasone furoate, refers to that product resulting in a smaller decline in $FEV_1$ over a defined period, for example 1 year, than the same product excluding fluticasone furoate (i.e the inhaled corticosteroid component). For example, if administration of a pharmaceutical product consisting of fluticasone furoate resulted in an $FEV_1$ decline of 20 ml/year and administration of placebo resulted in an $FEV_1$ decline of 45 ml/year, the pharmaceutical product comprising the inhaled corticosteroid (fluticasone furoate) will have reduced the rate of decline by 25 ml/year. In a further example, if administration of a pharmaceutical product comprising of fluticasone furoate and umeclidinium bromide resulted in an $FEV_1$ decline of 30 ml/year and administration of a pharmaceutical product consisting of umeclidinium bromide (i.e. same pharmaceutical product but without the corticosteroid component) resulted in an $FEV_1$ decline of 65 ml/year, the pharmaceutical product comprising the inhaled corticosteroid (fluticasone furoate) will have reduced the rate of decline by 35 ml/year.

In one embodiment, a pharmaceutical product of the invention reduces the rate of decline in lung function by between 10 to 19 ml/year, 20 to 29 ml/year, 30 to 39 ml/year, 40 to 49 ml/year, 50 to 59 ml/year, 60 to 69 ml/year, 70 to 79 ml/year, 80 to 89 ml/year, 90 to 99 ml/year, 100 to 109 ml/year, 110 to 119 ml/year, 120 to 129 ml/year, 130 to 139 ml/year, 140 to 149 ml/year, 150 to 159 ml/year, 160 to 169 ml/year, 170 to 179 ml/year, 180 to 189 ml/year or 190 to 199 ml/year. In one embodiment, a pharmaceutical product of the invention reduces the rate of decline in lung function by greater than about 5, 10, 15, 20, 25, 30, 35, 40, 45, 50, 55, 60, 70, 80, 90, 100, 125, 150, 175 or 200 ml/year.

As used herein, the term "blood eosinophil count" may refer to the number of eosinophils per microlitre (cells/μl) of blood. In one embodiment, the blood eosinophil count in a patient with COPD treated with a pharmaceutical product of the present invention is greater than 150 eosinophils/μl, for example, greater than 175/μl, 200 μl, 225 μl 250/μl, 275 μl, 300 μl, 350/μl, 450/μl, 500/μl, 750/μl or 1000/μl. COPD patients with a blood eosinophil count greater than, for example 75, 100, 125 cells/μl may also derive greater benefit from treatment with a pharmaceutical product of the present invention compared to patients with a blood eosinophil count below the selected level. The blood eosinophil count may also be expressed as the percentage of white blood cells, also known as leukocytes, in a blood sample that are eosinophils. The blood eosinophil count may be, for example, greater than 2%, 2.5%, 3%, 3.5% or 4%. In one embodiment, the blood eosinophil count in a patient with COPD treated with a pharmaceutical product of the present invention is greater than 2%. The blood eosinophil count can be manually or automatically calculated by methods well known in the art. Typically, a sample of blood is taken from a peripheral vein and analysed by an instrument (e.g. Automated Analyser) that provides the total number of white blood cells. All the white blood cell types can be provided as an absolute number per litre or percentage. A complete blood count with differential count also provides how many cells are eosinophils as an absolute value (cells/L or cells/μl of blood) or percentage of total white blood cells.

It will be appreciated by those skilled in the art that a blood eosinophil count calculated as a percentage can be converted to an eosinophil/μl value and vica versa. Moreover, either expression of the eosinophil count can be calculated and/or referred to as part of the uses and methods of the present invention.

In one aspect, a COPD patient's blood eosinophil count is calculated from the analysis of a single blood sample. In another aspect, a COPD patient's blood eosinophil count is an average value calculated from the analysis of multiple blood samples (e.g. 2, 3, 4, 5, 6, 7, 8, 9 or 10) taken over a period of time (e.g. one week or one-month).

As used herein, the term "pharmaceutical product" means the medicament that is used by the patient for the treatment of COPD. The term includes any device, such as an inhaler, or devices, that is/are required for delivery of the composition or compositions contained within that include the active therapeutic agents. A pharmaceutical product of the present invention comprising fluticasone furoate and optionally one or more therapeutic agents, may be any product that is capable of delivering the therapeutic agent(s) by the inhaled route. Furthermore, the pharmaceutical product may be more than one inhaler where, for example, the pharmaceutical product comprises two or more therapeutic agents and these are presented as separate compositions in different inhalers but intended to be used in combination for the treatment of COPD. A pharmaceutical product that contains two or more therapeutic agents can, however, be a single inhaler, wherein the two or more therapeutic agents are formulated in the same composition or presented in separate compositions within the same inhaler.

As used herein, the term "responder" refers to a COPD patient who through analysis has been identified as someone who will benefit from treatment with a pharmaceutical product of the present invention. A responder will also have a greater response to and derive greater benefit from treatment than a COPD patient who has been identified as a "non-responder". In the context of the present invention, a responder is a COPD patient who has a blood eosinophil count of ≥150 cells/μl or >2%, determined by analysis of a peripheral blood sample.

As used herein, the term "umeclidinium bromide" refers to 4-[hydroxy(diphenyl)methyl]-1-{2-[(phenylmethyl)oxy]ethyl}-1-azoniabicyclo[2.2.2]octane bromide, the long acting high-affinity pan-active muscarinic receptor antagonist which has potential for once-daily administration. Umeclidinium bromide in combination with vilanterol trifenatate has been approved in the US for the treatment of COPD. Umeclidinium bromide may be prepared as described in WO2005/104745/U.S. Pat. No. 7,488,827 (Example 84) or WO2014/027045, which are incorporated herein by reference. Umeclidinium bromide may be abbreviated to "UMEC".

As used herein, the term "vilanterol trifenatate" refers to 4-{(1R)-2-[(6-{2-[(2,6-dichlorobenzyl)oxy]ethoxy}hexyl)amino]-1-hydroxyethyl}-2-(hydroxymethyl)phenol triphenylacetate, the long-acting $beta_2$-agonist that provides sustained bronchodilation over a period of 24 hours or more and is suitable for once-daily administration. Vilanterol trifenatate may be prepared as described in WO2003/024439 (Example 78(i))/U.S. Pat. No. RE44874, which is incorporated herein by reference. Vilanterol trifenatate may be abbreviated to "VI".

The present invention is directed to pharmaceutical products comprising fluticasone furoate for use in the treatment of a subgroup of COPD patients. A subgroup of COPD patients of interest for the present invention are those have a blood eosinophil count ≥150 cells/μl since these patients may show an improved clinical response to treatment with a pharmaceutical product of the invention, compared to patients with a blood eosinophil count <150 cells/μl.

It will be appreciated by those skilled in the art that a patient's eosinophil count may alternatively be calculated or determined by analysis of an induced sputum sample rather than a blood sample. Therefore, the present invention is also directed to methods of treating COPD wherein instead of including a step directed to the calculation of a blood eosinophil count said method includes a step directed to the calculation of a sputum eosinophil count. Moreover, the present invention is also directed to uses of a pharmaceutical product comprising fluticasone furoate for the treatment of COPD, wherein the use refers to the patient having a sputum eosinophil count, for example >2%, rather than a blood eosinophil count.

COPD patients who have blood eosinophil count of for example ≥150 cell/μl or >2% may derive more benefit from treatment with an inhaled corticosteroid than those COPD patients that have lower levels of eosinophils. COPD patients with these higher levels of eosinophils treated with fluticasone furoate may, when compared with placebo, have improved $FEV_1$, improved Quality of Life (QoL) or health status determined by the CRQ or the SGRQ, improved dyspnea or a reduction in exacerbation frequency and severity.

Eosinophil level, for example blood eosinophil count, in stable COPD may predict the likely magnitude of the benefit of inhaled corticosteroid therapy, such as fluticasone furoate, in reducing the rate of moderate and/or severe COPD exacerbations. COPD patients with raised blood eosinophils may also have a greater risk of exacerbations. COPD patients with these higher levels of eosinophils treated with fluticasone furoate may, when compared with placebo or the same product absent the inhaled corticosteroid component, experience a reduction in COPD exacerbation frequency and/or severity.

In a first aspect, the present invention is directed to a pharmaceutical product comprising fluticasone furoate for use in the treatment of COPD in a patient, wherein the patient has a blood eosinophil count of ≥150 cells/μl.

In another aspect, the present invention is directed to a pharmaceutical product comprising fluticasone furoate for use in a method of treating COPD in a patient, wherein the patient has a blood eosinophil count of ≥150 cells/μl, and wherein the method comprises identifying that the patient has a blood eosinophil count of ≥150 cells/μl by analysis of a blood sample taken from said patient and then administering the pharmaceutical product comprising fluticasone furoate to the patient.

In a further aspect, the present invention is directed to a pharmaceutical product comprising fluticasone furoate for use in the treatment of COPD in a patient classified as a responder using a method comprising:
 a. calculating the number of eosinophils per microlitre of blood in a blood sample taken from a COPD patient;
 b. determining that the patient is a responder if the number of eosinophils in the blood sample is ≥150 cells/μl.

In a further aspect, the present invention is directed to a method of treating COPD in a patient comprising the steps of:
 a. calculating the eosinophils per microlitre (μl) of blood in a blood sample taken from a COPD patient;
 b. determining that the patient is a responder if the number of eosinophils in the blood sample is ≥150 cells/μl;
 c. administering a therapeutically effective amount of a pharmaceutical product comprising fluticasone furoate to said patient identified as a responder.

In a further aspect, the present invention is directed to the use of fluticasone furoate for the manufacture of a pharmaceutical product for the treatment of COPD in a patient, wherein the patient has a blood eosinophil count of ≥150 cells/μl.

In a further aspect, the present invention is directed to the use of fluticasone furoate for the manufacture of a pharmaceutical product for use in a method of treating COPD in a patient, wherein the patient has a blood eosinophil count of ≥150 cells/μl, and wherein the method comprises identifying that the patient has a blood eosinophil count of ≥150 cells/μl by analysis of a blood sample taken from said patient and then administering the pharmaceutical product comprising fluticasone furoate to the patient.

In a first aspect, the present invention is directed to a pharmaceutical product comprising fluticasone furoate for use in the treatment of COPD in a patient, wherein the patient has a blood eosinophil count of >2%.

In another aspect, the present invention is directed to a pharmaceutical product comprising fluticasone furoate for use in a method of treating COPD in a patient, wherein the patient has a blood eosinophil count >2%, and wherein the method comprises identifying that the patient has a blood eosinophil count >2% by analysis of a blood sample taken from said patient and then administering the pharmaceutical product comprising fluticasone furoate to the patient.

In a further aspect, the present invention is directed to a pharmaceutical product comprising fluticasone furoate for use in the treatment of COPD in a patient classified as a responder using a method comprising:
 a. calculating the percentage (%) of eosinophils in a blood sample taken from a COPD patient;

b. determining that the patient is a responder if the percentage of eosinophils in the blood sample is >2%.

In a further aspect, the present invention is directed to a method of treating COPD in a patient comprising the steps of:
- a. calculating the percentage (%) of eosinophils in a blood sample taken from a COPD patient;
- b. determining that the patient is a responder if the percentage of eosinophils in the blood sample is >2%;
- c. administering a therapeutically effective amount of a pharmaceutical product comprising fluticasone furoate to said patient identified as a responder.

In a further aspect, the present invention is directed to the use of fluticasone furoate for the manufacture of a pharmaceutical product for the treatment of COPD in a patient, wherein the patient has a blood eosinophil count of >2%.

In a further aspect, the present invention is directed to the use of fluticasone furoate for the manufacture of a pharmaceutical product for use in a method of treating COPD in a patient, wherein the patient has a blood eosinophil count >2%, and wherein the method comprises identifying that the patient has a blood eosinophil count >2% by analysis of a blood sample taken from said patient and then administering the pharmaceutical product comprising fluticasone furoate to the patient.

The present invention is directed to pharmaceutical products for the treatment of COPD. COPD is a chronic disease characterised by persistent airflow limitation that manifests as daily symptoms, such as dyspnea, chronic cough and a limitation in the patient's ability to perform daily activities. Chronic airflow limitation is caused by a mixture of small airways disease (obstructive bronchiolitis) and parenchymal destruction (emphysema). Furthermore, exacerbations of respiratory symptoms often occur in patients with COPD, triggered by a number of factors such as bacteria, virus and environmental pollutants. The GOLD strategy for the diagnosis, management and prevention of COPD (2014) states that once a patient has been diagnosed with COPD, there are two goals underpinning their treatment. The first goal is to reduce the patient's symptoms, i.e. relieve symptoms, improve health status and improve tolerance to exercise. The second goal is to reduce the patient's risk, meaning altering the progression of the disease, preventing and reducing severity of exacerbations or reducing mortality. The GOLD strategy states that prescription medicines are used to reduce symptoms, reduce frequency and severity of exacerbations and improve health status and exercise tolerance but that none of the existing treatments have been shown conclusively in clinical studies to modify the long-term decline in lung function that is characteristic of the disease. For example, one of the existing medicaments available is inhaled corticosteroids and the GOLD strategy states that various studies investigating the use of inhaled corticosteroids in the treatment of COPD have shown that "regular treatment with inhaled corticosteroids does not modify the long-term decline in $FEV_1$ nor mortality in patients with COPD".

There is, consequently, a need for further pharmacologic therapies that are able to modify the long-term decline in lung function seen in COPD patients, or a subgroup of COPD patients, and thus slow their disease progression.

The present invention provides such a therapy. In one embodiment, the present invention is directed to a pharmaceutical product comprising fluticasone furoate for use in the treatment of COPD in a patient, wherein the patient has a blood eosinophil count of ≥150 cells/µl, wherein the pharmaceutical product reduces the rate of decline in lung function in a COPD patient.

In a further embodiment, the present invention is directed to a pharmaceutical product comprising fluticasone furoate for use in a method for reducing the rate of decline in lung function COPD in a patient, wherein the patient has a blood eosinophil count of ≥150 cells/µl, and wherein the method comprises identifying that the patient has a blood eosinophil count of ≥150 cells/µl by analysis of a blood sample taken from said patient and then administering the pharmaceutical product comprising fluticasone furoate to the patient.

In a further embodiment, the present invention is directed to a pharmaceutical product comprising fluticasone furoate for use in reducing the rate of decline in lung function in a COPD patient classified as a responder using a method comprising:
- a. calculating the number of eosinophils per microlitre (µl) of blood in a blood sample taken from a COPD patient;
- b. determining that the patient is a responder if the number of eosinophils in the blood sample is ≥150 cells/µl.

In a further embodiment, the present invention is directed to a method of reducing the rate of decline in lung function in a patient with COPD comprising the steps of:
- a. calculating the number of eosinophils per microlitre (µl) of blood in a blood sample taken from a COPD patient;
- b. determining that the patient is a responder if the number of eosinophils in the blood sample is ≥150 cells/µl;
- c. administering a therapeutically effective amount of a pharmaceutical product comprising fluticasone furoate to said patient identified as a responder.

In a further embodiment, the present invention is directed to the use of fluticasone furoate for the manufacture of a pharmaceutical product for reducing the rate of decline in lung function in a patient with COPD, wherein the patient has a blood eosinophil count of ≥150 cells/µl.

In a further embodiment, the present invention is directed to the use of fluticasone furoate for the manufacture of a pharmaceutical product for reducing the rate of decline in lung function in a patient with COPD, wherein the patient has a blood eosinophil count of ≥150 cells/µl, and wherein the method comprises identifying that the patient has a blood eosinophil count of >150 cells/µl by analysis of a blood sample taken from said patient and then administering the pharmaceutical product comprising fluticasone furoate to the patient.

In one embodiment, the present invention is directed to a pharmaceutical product comprising fluticasone furoate for use in the treatment of COPD in a patient, wherein the patient has a blood eosinophil count of >2%, wherein the pharmaceutical product reduces the rate of decline in lung function in a COPD patient.

In a further embodiment, the present invention is directed to a pharmaceutical product comprising fluticasone furoate for use in a method for reducing the rate of decline in lung function COPD in a patient, wherein the patient has a blood eosinophil count >2%, and wherein the method comprises identifying that the patient has a blood eosinophil count >2% by analysis of a blood sample taken from said patient and then administering the pharmaceutical product comprising fluticasone furoate to the patient.

In a further embodiment, the present invention is directed to a pharmaceutical product comprising fluticasone furoate for use in reducing the rate of decline in lung function in a COPD patient classified as a responder using a method comprising:
  a. calculating the percentage (%) of eosinophils in a blood sample taken from a COPD patient;
  b. determining that the patient is a responder if the percentage of eosinophils in the blood sample is >2%.

In a further embodiment, the present invention is directed to a method of reducing the rate of decline in lung function in a patient with COPD comprising the steps of:
  a. calculating the percentage (%) of eosinophils in a blood sample taken from a COPD patient;
  b. determining that the patient is a responder if the percentage of eosinophils in the blood sample is >2%;
  c. administering a therapeutically effective amount of a pharmaceutical product comprising fluticasone furoate to said patient identified as a responder.

In a further embodiment, the present invention is directed to the use of fluticasone furoate for the manufacture of a pharmaceutical product for reducing the rate of decline in lung function in a patient with COPD, wherein the patient has a blood eosinophil count of >2%.

In a further embodiment, the present invention is directed to the use of fluticasone furoate for the manufacture of a pharmaceutical product for reducing the rate of decline in lung function in a patient with COPD, wherein the patient has a blood eosinophil count >2%, and wherein the method comprises identifying that the patient has a blood eosinophil count >2% by analysis of a blood sample taken from said patient and then administering the pharmaceutical product comprising fluticasone furoate to the patient.

Pharmaceutical products of the present invention may contain fluticasone furoate as the sole active therapeutic agent. Alternatively, pharmaceutical products of the present invention may comprise one or more further therapeutic agents in addition to the inhaled corticosteroid, fluticasone furoate. Further therapeutic agents may include bronchodilators, for example, beta$_2$-agonists, such as vilanterol trifenatate; and muscarinic antagonists, such as umeclidinium bromide. In one embodiment, the pharmaceutical product of the present invention further comprises umeclidinium bromide. In another embodiment, the pharmaceutical product further comprises vilanterol trifenatate. In yet a further embodiment, the pharmaceutical product further comprises vilanterol trifenatate and umeclidinium bromide.

In a further embodiment, the present invention is directed to a pharmaceutical product comprising fluticasone furoate, umeclidinium bromide and vilanterol trifenatate for use in the treatment of COPD in a patient, wherein the patient has a blood eosinophil count of ≥150 cells/µl, wherein the pharmaceutical product reduces the rate of decline in lung function in a COPD patient.

In a further embodiment, the present invention is directed to a pharmaceutical product comprising fluticasone furoate, umeclidinium bromide and vilanterol trifenatate for use in a method for reducing the rate of decline in lung function COPD in a patient, wherein the patient has a blood eosinophil count of ≥150 cells/µl, and wherein the method comprises identifying that the patient has a blood eosinophil count of ≥150 cells/µl by analysis of a blood sample taken from said patient and then administering the pharmaceutical product to the patient.

In a further embodiment, the present invention is directed to a pharmaceutical product comprising fluticasone furoate, umeclidinium bromide and vilanterol trifenatate for use in reducing the rate of decline in lung function in a COPD patient classified as a responder using a method comprising:
  a. calculating the number of eosinophils per microlitre of blood in a blood sample taken from a COPD patient;
  b. determining that the patient is a responder if the number of eosinophils per microlitre of blood in the blood sample is ≥150 cells/µl.

In a further embodiment, the present invention is directed to a method of reducing the rate of decline in lung function in a patient with COPD comprising the steps of:
  a. calculating the number of eosinophils per microlitre of blood in a blood sample taken from a COPD patient;
  b. determining that the patient is a responder if the number of eosinophils per microlitre of blood in the blood sample is ≥150 cells/µl;
  c. administering a therapeutically effective amount of a pharmaceutical product comprising fluticasone furoate, umeclidinium bromide and vilanterol trifenatate to said patient identified as a responder.

A pharmaceutical product of the present invention comprising fluticasone furoate and optionally one or more therapeutic agents, may be any product that is capable of delivering the therapeutic agent(s) by the inhaled route. For example, the pharmaceutical product may be a reservoir dry powder inhaler, unit-dose dry powder inhaler, pre-metered multi-dose dry powder inhaler, pressurised metered dose inhaler or a nebuliser. Furthermore, the pharmaceutical product may be more than one inhaler where, for example, the pharmaceutical product comprises two or more therapeutic agents and these are presented as separate compositions in different inhalers but intended to be used in combination for the treatment of COPD. A pharmaceutical product that contains two or more therapeutic agents can, however, be a single inhaler, wherein the two or more therapeutic agents are formulated in the same composition or presented in separate compositions within the same inhaler. Separate presentation within the same inhaler enables therapy to be administered sequentially or simultaneously.

When the pharmaceutical product of the present invention comprising fluticasone furoate additionally includes umeclidinium bromide, this additional agent may be formulated separately from fluticasone furoate and presented for either sequential or simultaneous administration or may be admixed with fluticasone furoate and presented in the same composition. The same is true for vilanterol trifenatate.

When the pharmaceutical product of the present invention comprises fluticasone furoate, umeclidinium bromide and vilanterol trifenatate, these three therapeutic agents may be formulated separately and presented for either sequential or simultaneous administration or they may be admixed and presented in the same composition. In another option, two therapeutic agents may be admixed and presented in the same composition with the third therapeutic agent presented in a second composition. For example, umeclidinium bromide and vilanterol trifenatate may be admixed together in the same composition with fluticasone furoate presented in a separate composition.

In one embodiment, the pharmaceutical product is a dry powder inhaler.

A dry powder inhaler may include one or more, for example two, dry powder compositions. A dry powder composition will typically include the therapeutic agent(s) formulated with one or more carriers and/or excipients, but compositions consisting of just the therapeutic agent(s) are within the ambit of this invention.

Dry powder compositions as described herein may be provided in bulk, in the reservoir of reservoir-type inhalation devices. Such reservoir-devices are provided with a metering mechanism for metering a dose of the composition from the bulk in the reservoir, and exposing the metered dose in an inhalation channel, where the metered dose is able to be inhaled by a patient inhaling at a mouthpiece of the device. Exemplary marketed devices of this type are TURBU-HALER™ of AstraZeneca, TWISTHALER™ of Schering and CLICKHALER™ of Innovata.

In a further embodiment, a dry powder composition suitable for inhaled administration may be incorporated into a plurality of sealed dose containers provided on medicament pack(s) mounted inside a suitable inhalation device. The containers may be rupturable, peelable or otherwise openable one-at-a-time and the doses of the dry powder composition administered by inhalation on a mouthpiece of the inhalation device, as known in the art. The medicament pack may take a number of different forms, for instance a disk-shape or an elongate strip. Representative inhalation devices are the DISKHALER™, DISKUS™ and ELLIPTA™ devices, marketed by GSK. The DISKUS™ inhalation device is, for example, described in GB 2242134A/U.S. Pat. No. 5,873,360.

A further delivery method for a dry powder inhalable composition is for metered doses of the composition to be provided in capsules (one dose per capsule) which are then loaded into an inhalation device, typically by the patient on demand. The device has means to rupture, pierce or otherwise open the capsule so that the dose is able to be entrained into the patient's lung when they inhale at the device mouthpiece. ROTAHALER™ of GSK and HANDI-HALER™ of Boehringer Ingelheim are examples of such devices.

A dry powder composition may also be presented in an inhaled delivery device which permits separate containment of therapeutic agents optionally in admixture with one or more carriers and/or excipients. Thus, for example, the individual therapeutic agents of the pharmaceutical product of the present invention are administrable simultaneously but are stored separately, e.g. in separate pharmaceutical compositions, for example as described in WO 2003/061743 A1/US2007-0062525, WO 2007/012871 A1/US2008-0196718 and/or WO2007/068896/U.S. Pat. No. 8,534,281. In one embodiment, a delivery device permitting separate containment of the therapeutic agents has two medicament packs in peelable blister strip form, each pack containing pre-metered doses in blister pockets arranged along its length. Said device has an internal indexing mechanism which, each time the device is actuated, peels opens a pocket of each strip and positions the packs so that each newly exposed dose of each pack is adjacent a manifold which communicates with a mouthpiece of the device. When the patient inhales at the mouthpiece, each dose is simultaneously drawn out of its associated pocket into the manifold and entrained via the mouthpiece into the patient's respiratory tract. Thus, each time the device is used, the patient is administered a combination therapy consisting of a dose from each medicament pack. DUGHALER™ of Innovata and ELLIPTA™ of GSK permit separate containment of multiple therapeutic agents in the same inhaler device.

In a further embodiment, the pharmaceutical product is a dry powder inhaler comprising a dry powder composition comprising fluticasone furoate and a pharmaceutically acceptable carrier.

In a further embodiment, the pharmaceutical product is a dry powder inhaler comprising a first dry powder composition comprising fluticasone furoate and optionally one or more pharmaceutically acceptable carriers and/or excipients, and a second dry powder composition comprising umeclidinium bromide and optionally one or more pharmaceutically acceptable carriers and/or excipients.

In a further embodiment, the pharmaceutical product is a dry powder inhaler comprising a first dry powder composition comprising fluticasone furoate and optionally one or more pharmaceutically acceptable carriers and/or excipients, and a second dry powder composition comprising vilanterol trifenatate and optionally one or more pharmaceutically acceptable carriers and/or excipients.

In a further embodiment, the pharmaceutical product is a dry powder inhaler comprising a first dry powder composition comprising fluticasone furoate and optionally one or more pharmaceutically acceptable carriers and/or excipients, and a second dry powder composition comprising umeclidinium bromide, vilanterol trifenatate and optionally one or more pharmaceutically acceptable carriers and/or excipients.

Dry powder compositions for delivery via a dry powder inhaler may be presented in unit dosage form, for example, in capsules, cartridges or blisters made from, for example, laminated aluminium foil. In a further embodiment, each unit dose may contain, for example, 50, 100, 200, 250 mcg of fluticasone furoate. In a further embodiment, each unit dose may contain 100 mcg of fluticasone furoate.

If a pharmaceutical product of the present invention additionally comprises umeclidinium bromide, each unit dose may contain, for example, 15.625 mcg, 31.25 mcg, 62.5 mcg or 125 mcg of the free cation. In a further embodiment, each unit dose may contain 62.5 mcg of umeclidinium bromide calculated as the amount of free cation rather than the salt.

If a pharmaceutical product of the present invention additionally comprises vilanterol trifenatate, each unit dose may contain, for example, 3 mcg, 6.25 mcg, 12.5 mcg, 25 mcg, 50 mcg or 100 mcg of the free base. In a further embodiment, each unit dose may contain 25 mcg of vilanterol trifenatate calculated as the amount of free base rather than the triphenylacetate salt.

In a further embodiment, the present invention is directed to a dry powder inhaler comprising two dry powder compositions, the first dry powder composition comprising fluticasone furoate in an amount of about 100 mcg/dose and the second dry powder composition comprising umeclidinium bromide in an amount of about 62.5 mcg/dose or 125 mcg/dose and/or vilanterol trifenatate in an amount of about 25 mcg/dose for use in the treatment of COPD in a patient, wherein the patient has a blood eosinophil count of ≥150 cells/µl, wherein the dry powder inhaler reduces the rate of decline in lung function in a COPD patient.

In a further embodiment, the present invention is directed to a dry powder inhaler comprising a dry powder inhaler comprising two dry powder compositions, the first dry powder composition comprising fluticasone furoate in an amount of about 100 mcg/dose and the second dry powder composition comprising umeclidinium bromide in an amount of about 62.5 mcg/dose or 125 mcg/dose and/or vilanterol trifenatate in an amount of about 25 mcg/dose for use in a method for reducing the rate of decline in lung function COPD in a patient, wherein the patient has a blood eosinophil count of ≥150 cells/µl, and wherein the method comprises identifying that the patient has a blood eosinophil count of ≥150 cells/µl by analysis of a blood sample taken from said patient and then administering the dry powder inhaler to the patient.

In a further embodiment, the present invention is directed to a dry powder inhaler comprising two dry powder compositions, the first dry powder composition comprising fluticasone furoate in an amount of about 100 mcg/dose and the second dry powder composition comprising umeclidinium bromide in an amount of about 62.5 mcg/dose or 125 mcg/dose and/or vilanterol trifenatate in an amount of about 25 mcg/dose for use in reducing the rate of decline in lung function in a COPD patient classified as a responder using a method comprising:
  a. calculating the number of eosinophils per microlitre of blood in a blood sample taken from a COPD patient;
  b. determining that the patient is a responder if the number of eosinophils in the blood sample is ≥150 cells/µl.

In a further embodiment, the present invention is directed to a method of reducing the rate of decline in lung function in a patient with COPD comprising the steps of:
  a. calculating the number of eosinophils per microlitre of blood in a blood sample taken from a COPD patient;
  b. determining that the patient is a responder if the number of eosinophils in the blood sample is ≥150 cells/µl;
    administering a therapeutically effective amount of a dry powder inhaler comprising two dry powder compositions, the first dry powder composition comprising fluticasone furoate in an amount of about 100 mcg/dose and the second dry powder composition comprising umeclidinium bromide in an amount of about 62.5 mcg/dose or 125 mcg/dose and/or vilanterol trifenatate in an amount of about 25 mcg/dose to said patient identified as a responder.

Dry powder compositions may comprise a carrier. The carrier when it is lactose e.g. α-lactose monohydrate, may form from about 91 to about 99%, e.g. 97.7-99.0% or 91.0-99.2% by weight of the formulation. In general, the particle size of the carrier, for example lactose, will be much greater than the inhaled therapeutic agents(s) within the dry powder composition. When the carrier is lactose it will typically be present as milled lactose, having a MMD (mass median diameter) of 60-90 µm. Active ingredients, for example fluticasone furoate, for administration by inhalation desirably have a controlled particle size. The optimum particle size for inhalation into the bronchial system is usually 1-10 µm, preferably 2-5 µm. Particles having a size above 20 µm are generally too large when inhaled to reach the small airways. To achieve these particle sizes the particles of the active ingredient as produced may be size reduced by conventional means e.g. by micronization. The desired fraction may be separated out by air classification or sieving. Preferably, the particles will be crystalline.

The lactose component may comprise a fine lactose fraction. The 'fine' lactose fraction is defined as the fraction of lactose having a particle size of less than 7 µm, such as less than 6 µm, for example less than 5 µm. The particle size of the 'fine' lactose fraction may be less than 4.5 µm. The fine lactose fraction, if present, may comprise 2 to 10% by weight of the total lactose component, such as 3 to 6% by weight fine lactose, for example 4.5% by weight fine lactose.

Dry powder compositions may also include, in addition to the active ingredient and carrier, a further excipient (eg a ternary agent) such as a sugar ester, calcium stearate or magnesium stearate. Magnesium stearate, if present in the composition, is generally used in an amount of about 0.2 to 2%, e.g. 0.6 to 2% or 0.5 to 1.75%, e.g. 0.6%, 0.75%, 1%, 1.25% or 1.5% w/w, based on the total weight of the composition. The magnesium stearate will typically have a particle size in the range 1 to 50 µm, and more particularly 1-20 µm, e.g. 1-10 µm. Commercial sources of magnesium stearate include Peter Greven, Covidien/Mallinckodt and FACI.

In a further embodiment, the present invention is directed to a dry powder inhaler comprising two dry powder compositions, the first dry powder composition comprising:
  a. fluticasone furoate in an amount of about 100 mcg/dose, and
  b. lactose;
and the second dry powder composition comprising:
  a. umeclidinium bromide in an amount of about 62.5 mcg/dose, and
  b. vilanterol trifenatate in an amount of about 25 mcg/dose, and
  c. lactose, and
  d. magnesium stearate in an amount of about 0.6% w/w;
for use in the treatment of COPD in a patient, wherein the patient has a blood eosinophil count of ≥150 cells/µl, wherein the dry powder inhaler reduces the rate of decline in lung function in a COPD patient.

In a further embodiment, the present invention is directed to a dry powder inhaler comprising two dry powder compositions, the first dry powder composition comprising:
  a. fluticasone furoate in an amount of about 100 mcg/dose, and
  b. lactose;
and the second dry powder composition comprising:
  a. umeclidinium bromide in an amount of about 62.5 mcg/dose, and
  b. vilanterol trifenatate in an amount of about 25 mcg/dose, and
  c. lactose, and
  d. magnesium stearate in an amount of about 0.6% w/w;
for use in a method for reducing the rate of decline in lung function COPD in a patient, wherein the patient has a blood eosinophil count of ≥150 cells/µl, and wherein the method comprises identifying that the patient has a blood eosinophil count of ≥150 cells/µl by analysis of a blood sample taken from said patient and then administering the dry powder inhaler to the patient.

In a further embodiment, the present invention is directed to a dry powder inhaler comprising two dry powder compositions, the first dry powder composition comprising:
  a. fluticasone furoate in an amount of about 100 mg/dose, and
  b. lactose;
and the second dry powder composition comprising:
  a. umeclidinium bromide in an amount of about 62.5 mcg/dose, and
  b. vilanterol trifenatate in an amount of about 25 mcg/dose, and
  c. lactose, and
  d. magnesium stearate in an amount of about 0.6% w/w;
for use in reducing the rate of decline in lung function in a COPD patient classified as a responder using a method comprising:
  a. calculating the number of eosinophils per microlitre of blood in a blood sample taken from a COPD patient;
  b. determining that the patient is a responder if the number of eosinophils in the blood sample is ≥150 cells/µl.

In a further embodiment, the present invention is directed to a method of reducing the rate of decline in lung function in a patient with COPD comprising the steps of:
  a. calculating the number of eosinophils per microlitre of blood in a blood sample taken from a COPD patient;
  b. determining that the patient is a responder if the number of eosinophils in the blood sample is ≥150 cells/µl;

administering a therapeutically effective amount of a dry powder inhaler comprising two dry powder compositions, the first dry powder composition comprising:
  a. fluticasone furoate in an amount of about 100 mcg/dose, and
  b. lactose;
and the second dry powder composition comprising:
  a. umeclidinium bromide in an amount of about 62.5 mcg/dose, and
  b. vilanterol trifenatate in an amount of about 25 mcg/dose, and
  c. lactose, and
  d. magnesium stearate in an amount of about 0.6% w/w;
to said patient identified as a responder.

EXAMPLE 1

Re-Analysis of Clinical Study Data

Methods: The results of ISOLDE (Burge P S et al BMJ 2000; 320:1297-303), a 3-year study of the effects of fluticasone propionate (FP) 500 mcg twice daily on rate of decline of $FEV_1$ in well-characterised COPD patients were re-analysed by baseline blood eosinophil count (≥2%, <2%).

Results: The pre-specified analysis of ISOLDE showed no effect of FP on the rate of decline of $FEV_1$ for FP vs. placebo. Eosinophil count was <2% in 68% of patients; the spirometric characteristics of these patients were similar to those with an eosinophil count ≥2%. Patients with an eosinophil count <2% showed no difference in rate of decline of $FEV_1$ with FP vs. placebo (figure). In patients with an eosinophil count ≥2%, FP 500 mcg slowed the rate of decline of lung function by 38 mL per year compared with placebo (p=0.001).

Conclusion: A baseline blood eosinophil count of ≥2% identifies a group of COPD patients who show a slower rate of decline of $FEV_1$ when treated with inhaled corticosteroids.

EXAMPLE 2

Clinical Study

A 52-week, randomised, double-blind, 3-arm parallel group_clinical study is performed to compare the efficacy, safety and tolerability of the fixed dose triple combination FF/UMEC/VI with the fixed dose dual combinations of FF/VI and UMEC/VI, all given once daily in the morning via a dry powder inhaler in subjects with COPD.

The treatment groups:

FF/UMEC/VI 100 mcg/62.5 mcg/25 mcg

FF/VI 100 mcg/25 mcg

UMEC/VI 62.5 mcg/25 mcg

The primary objective is to evaluate the efficacy of FF/UMEC/VI to reduce the annual rate of moderate and severe exacerbations compared with dual therapy of FF/VI or UMEC/VI in subjects with COPD. A secondary objective is to evaluate the efficacy of FF/UMEC/VI to reduce exacerbations compared with UMEC/VI in the subset of subjects with a blood eosinophil count ≥150 cells/μl. An extension of the above study is performed with the primary objective of assessing the rate of decline in $FEV_1$ for FF/UMEC/VI versus UMEC/VI in the high eosinophil group (≥150 cells/μl).

EXAMPLE 3

Post-Hoc Analysis of Clinical Study Data

Fluticasone furoate (FF)/vilanterol (VI) reduces COPD exacerbations when compared with treatment with VI alone. Identification of a simple biomarker would allow targeted treatment. The objective of this post-hoc analysis of clinical study data was to compare exacerbation rates between FF/VI and VI in patients with moderate to very severe COPD, stratified by blood eosinophil level.

Methods: We evaluated the use of blood eosinophil count through post-hoc analysis of pooled data from two randomised, double-blind, placebo-controlled 1-year trials (Dransfield M T et al, Lancet Resp Med 2013; 1:210-23) comparing FF/VI (50/25 mcg, 100/25 mcg or 200/25 mcg once daily) to VI (25 mcg once daily) in patients with COPD and a history of exacerbations in the last year. We evaluated the FF-related reduction in exacerbation rates in patients with eosinophil counts <2% and ≥2%.

Results: 3177 patients provided blood samples at study entry; 2083 (66%) had eosinophils ≥2%. Exacerbation rates were higher in the subgroup treated with VI alone (1.28 vs 0.91/patient/yr). Baseline eosinophil count was significantly associated with reduced exacerbation rates with the three doses of FF/VI combined. Exacerbations were reduced by 29% (p<0.001) in patients with eosinophils ≥2% and 10% (p=0.283) in those with <2%. Treatment differential increased with increasing FF dose. In patients with eosinophils ≥2% receiving FF/VI 50/25 mcg, 100/25 mcg and 200/25 mcg, exacerbations reductions were, respectively: 21%, 33%, 33% (all p<0.01). For eosinophils <2%, the corresponding reductions were 9%, 18%, 3%.

Conclusion: Blood eosinophil level is a promising biomarker of response for inhaled corticosteroid (ICS) treatment in patients with COPD.

The invention claimed is:

1. A method of reducing the rate of decline in lung function in a human patient with stable COPD comprising:
   a. determining the blood eosinophil count of the human patient, and,
   b. where the patient has a blood eosinophil count of ≥150 cells/μL, administering to the patient an inhaled pharmaceutical product comprising fluticasone furoate.

2. The method of claim 1, wherein step a. comprises the analysis of a blood sample taken from said patient.

3. The method of claim 1, wherein step a. comprises:
   i. calculating the number of eosinophils per microlitre of blood in a blood sample taken from said patient; and
   ii. determining that said patient is a responder if the number of eosinophils in the blood sample is ≥150 cells/μL.

4. The method of claim 1, wherein the inhaled pharmaceutical product comprises a dry powder inhaler comprising one or more dry powder compositions.

5. The method of claim 4, wherein said one or more dry powder compositions are in unit-dose form.

6. The method of claim 5, wherein fluticasone furoate is present in an amount of about 100 mcg/dose.

7. The method of claim 6, wherein the inhaled pharmaceutical product further comprises lactose monohydrate.

8. The method of claim 1, wherein the inhaled pharmaceutical product further comprises umeclidinium bromide.

9. The method of claim 8, wherein the inhaled pharmaceutical product comprises a dry powder inhaler, wherein said dry powder inhaler comprises one or more dry powder compositions.

10. The method of claim 9, wherein said one or more dry powder compisitions are present in unit-dose form.

11. The method of claim 10, wherein said fluticasone furoate is present in an amount of about 100 mcg/dose, and said umeclidinium bromide is present in an amount of about 62.5 mcg (of the free cation)/dose or 125 mcg (of the free cation)/dose.

12. The method of claim 10, wherein said one or more dry powder compositions comprises a first and a second dry powder composition, each in unit dose form, wherein
said first dry powder composition comprises said fluticasone furoate in an amount of about 100 mcg/dose; and;
said second dry powder composition comprises said umeclidinium bromide in an amount of about 62.5 mcg (of the free cation)/dose or 125 mcg (of the free cation)/dose.

13. The method of claim 12, wherein said first dry powder composition comprises said fluticasone furoate and lactose monohydrate, and said second dry powder composition comprises said umeclidinium bromide and further comprises lactose monohydrate, and magnesium stearate.

14. The method of claim 13, wherein said magnesium stearate is present in an amount of 0.6% w/w of said second composition.

15. The method of claim 13, wherein said first and second compositions in unit dose form are presented for simultaneous administration.

16. The method of claim 1, wherein the inhaled pharmaceutical product further comprises vilanterol trifenatate.

17. The method of claim 16, wherein the inhaled pharmaceutical product comprises a dry powder inhaler, said dry powder inhaler comprising one or more dry powder compositions.

18. The method of claim 17, wherein said one or more dry powder compositions are present in unit-dose form.

19. The method of claim 18, wherein said fluticasone furoate is present in an amount of about 100 mcg/dose, and said vilanterol trifenatate is present in an amount of about 25 mcg (of the free base)/dose.

20. The method of claim 19, wherein said dry powder inhaler comprises a first and a second dry powder composition,
said first dry powder composition comprising said fluticasone furoate in an amount of about 100 mcg/dose, and;
said second dry powder composition comprising said vilanterol trifenatate is in an amount of about 25 mcg (of the free base)/dose.

21. The method of claim 20, wherein said first dry powder composition further comprises lactose monohydrate; and said second dry powder composition further comprises lactose monohydrate and magnesium stearate.

22. The method of claim 21, wherein said magnesium stearate is present in an amount of 0.6% w/w of the second composition.

23. The method of claim 21, wherein said first and second dry powder compositions are in unit dose form and are presented for simultaneous administration.

24. The method of claim 1, wherein the inhaled pharmaceutical product further comprises umeclidinium bromide and vilanterol trifenatate.

25. The method of claim 24, wherein the inhaled pharmaceutical product comprises a dry powder inhaler, wherein said dry powder inhaler comprising one or more dry powder compositions.

26. The method of claim 25, wherein said one or more dry powder compositions are in unit-dose form.

27. The method of claim 26, wherein said fluticasone furoate is present in an amount of about 100 mcg/dose, said umeclidinium bromide is in an amount of about 62.5 mcg (of the free cation)/dose or 125 mcg (of the free cation)/dose, and said vilanterol trifenatate is in an amount of about 25 mcg (of the free base)/dose.

28. The method of claim 27, wherein the dry powder inhaler comprises a first and a second dry powder composition,
said first dry powder composition comprising said fluticasone furoate in an amount of about 100 mcg/dose, and;
said second dry powder composition comprising said umeclidinium bromide in an amount of about 62.5 mcg (of the free cation)/dose or 125 mcg (of the free cation)/dose and said vilanterol trifenatate in an amount of about 25 mcg (of the free base)/dose.

29. The method of claim 28, wherein said first dry powder composition further comprises lactose monohydrate; and said second dry powder composition further comprises lactose monohydrate and magnesium stearate.

30. The method of claim 29, wherein said magnesium stearate is present in an amount of 0.6% w/w of the second composition.

31. The method of claim 29, wherein said first and second dry powder compositions are in unit dose form and are presented for simultaneous administration.

* * * * *